United States Patent
Arno

(10) Patent No.: US 7,011,614 B2
(45) Date of Patent: Mar. 14, 2006

(54) INFRARED THERMOPILE DETECTOR SYSTEM FOR SEMICONDUCTOR PROCESS MONITORING AND CONTROL

(75) Inventor: Jose Arno, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 116 days.

(21) Appl. No.: 10/623,244

(22) Filed: Jul. 18, 2003

(65) Prior Publication Data

US 2004/0018746 A1 Jan. 29, 2004

Related U.S. Application Data

(62) Division of application No. 10/140,848, filed on May 8, 2002, now Pat. No. 6,617,175.

(51) Int. Cl.
*G01R 31/26* (2006.01)
(52) U.S. Cl. ..................... 483/14; 73/204.15
(58) Field of Classification Search ............. 73/204.15; 250/343; 438/14
See application file for complete search history.

(56) References Cited

U.S. PATENT DOCUMENTS

| | | | |
|---|---|---|---|
| 4,935,345 A | | 6/1990 | Guilbeau |
| 5,047,352 A | | 9/1991 | Stetter et al. |
| 5,282,473 A | * | 2/1994 | Braig et al. .................. 600/532 |
| 5,464,983 A | * | 11/1995 | Wang .......................... 250/343 |
| 5,589,689 A | | 12/1996 | Koskinen |
| 5,650,624 A | | 7/1997 | Wong |
| 5,721,430 A | | 2/1998 | Wong |
| 5,834,777 A | | 11/1998 | Wong |
| 6,348,650 B1 | | 2/2002 | Endo et al. |
| 6,370,950 B1 | * | 4/2002 | Lammerink .............. 73/204.15 |
| 6,469,303 B1 | | 10/2002 | Sun et al. |

OTHER PUBLICATIONS

IEEE 100, "The Authoritative Dictionary of IEEE Standards Terms", Seventh Edition ISBN 0-7381-2601-2, page#1174.*
Application Note of Thermopile IR Sensors, (Rev.02), Thermometrics Global Business, pp. 1-9, and attachment pages, Sep. 1999.
Paul A. Wilks, Wilks Enterprise, "The Birth of Infrared Filometry", Spectroscopy SHOWCASE, Guest Editorial, p. 14, Mar. 2002.
Jurgen Schilz, Perkin Elmer Optoelectronics, Applications of Thermoelectric Infrared Sensors (Thermopiles): Gas Detection by Infrared Absorption; NDIR, pp. 1-11.
Peter Adrian, Sensor Business Digest, Vital Information Publication, Sensor Business Digest Sensor Industry Developments and Trends, Oct. 2001.

* cited by examiner

*Primary Examiner*—Michael Lebentritt
*Assistant Examiner*—Andre' Stevenson
(74) *Attorney, Agent, or Firm*—Steven J. Hultquist; Intellectual Property/Technology Law

(57) ABSTRACT

A thermopile-based detector for monitoring and/or controlling semiconductor processes, and a method of monitoring and/or controlling semiconductor processes using thermopile-based sensing of conditions in and/or affecting such processes.

16 Claims, 5 Drawing Sheets

INFRARED THERMOPILE DETECTOR SYSTEM FOR SEMICONDUCTOR PROCESS MONITORING AND CONTROL

This is a Divisional of U.S. application Ser. No. 10/140,848, filed on May 8, 2002, U.S. Pat. No. 6,617,175.

BACKGROUND OF THE INVENTION

1. Field of the Invention

This invention relates to infrared thermopile systems for semiconductor process monitoring and control, and to a method of monitoring and controlling semiconductor processes using infrared thermopile sensing of conditions in and/or affecting such processes.

2. Description of the Related Art

Sensors and monitoring devices used in the semiconductor industry generally have two purposes. One type of such device is used as a safety sensor to warn persons (e.g., personnel operating the semiconductor process equipment or otherwise in proximity to such equipment) of the presence of toxic or otherwise hazardous materials associated with the process in the ambient environment of the process system. These safety sensors, sometimes termed "life safety sensors," have lower detection limits consistent with the threshold limit values (TLVs) of the gases and vapors to be detected. By way of example, an arsine gas safety sensor may have a lower detection limit of 50 parts per billion by volume (ppbv), so that any concentration of arsine that is 50 ppbv or higher will be sensed by the safety sensor device.

The other purpose for which sensors and monitoring devices have been used in the semiconductor industry is controlling semiconductor process. Examples include $SiF_4$ ultraviolet (UV) emission detectors that are used to provide a signal indicative of the completion of chamber cleaning operations.

The semiconductor manufacturing field continues to seek improvements in process monitoring and control.

SUMMARY OF THE INVENTION

The present invention relates to infrared thermopile systems for semiconductor process monitoring and control, and to a method of monitoring and controlling semiconductor processes using infrared thermopile sensing of conditions in and/or affecting such processes.

In one aspect, the present invention relates to a semiconductor process system including flow circuitry for flow of a process gas. The system comprises:

a gas sampling region for the process gas;

an infrared radiation source constructed and arranged to transmit infrared radiation through the gas sampling region;

a thermopile detector constructed and arranged to receive infrared radiation after the transmission thereof through the gas sampling region and to responsively generate an output signal correlative of concentration of at least one selected component of the process gas; and process control means arranged to receive the output of the thermopile detector and to responsively control one or more process conditions in and/or affecting the semiconductor process system.

In another aspect, the invention relates to a method of operating a semiconductor process including processing of or with a gas, said method comprising sensing concentration of a desired component of said gas with a thermopile detector, generating an output from said thermopile detector indicative of concentration of said selected component of said gas, and controlling one or more conditions in and/or affecting the semiconductor process, in response to said output.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
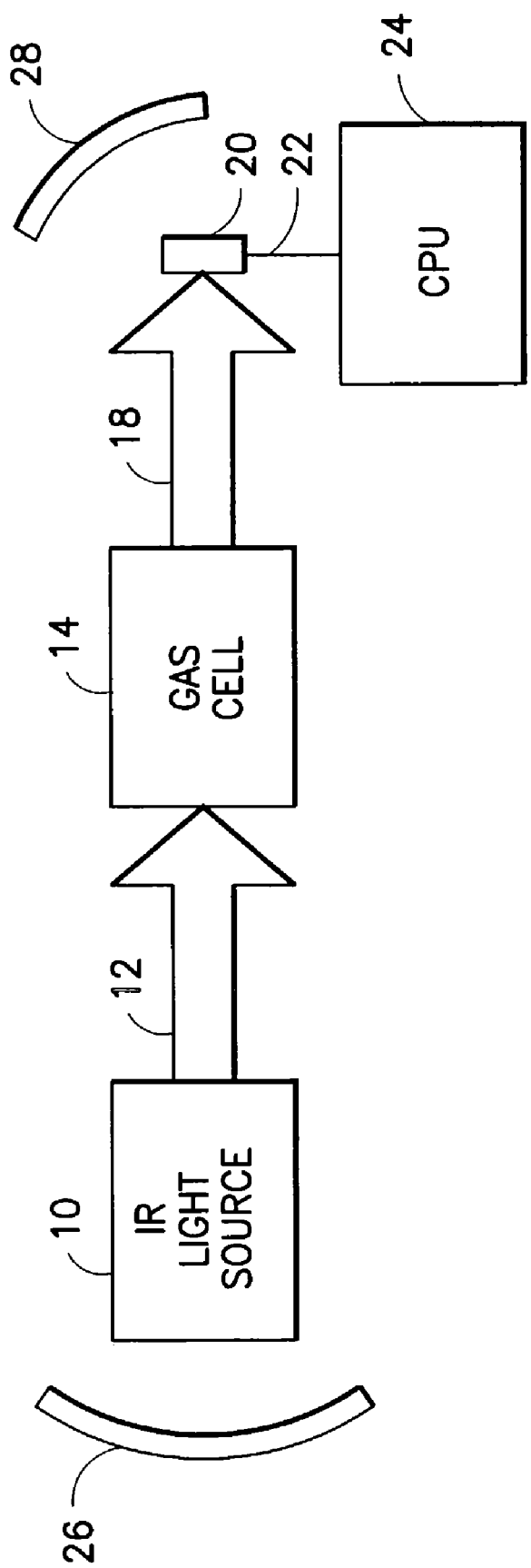
FIG. 1 is a schematic representation of a thermopile detector system.

The present invention provides an infrared thermopile detector system useful for semiconductor process monitoring and control, and a method of monitoring and/or controlling semiconductor processes using infrared thermopile sensing of conditions in and/or affecting such processes.

As used herein, the term "semiconductor process" is intended to be broadly construed to include any and all processing and unit operations involved in the manufacture of semiconductor products, as well as all operations involving treatment or processing of materials used in or produced by a semiconductor manufacturing facility, as well as all operations carried out in connection with the semiconductor manufacturing facility not involving active manufacturing (examples include conditioning of process equipment, purging of chemical delivery lines in preparation for operation, etch cleaning of process tool chambers, abatement of toxic or hazardous gases from effluents produced by the semiconductor manufacturing facility, etc.).

The operation of the infrared detection system of the invention is based on the fact that most infrared energy-absorbing molecules absorb infrared radiation at discrete energy levels, so that when a gas, liquid or solid composition is exposed to a broad wavelength infrared radiation, the infrared energy-absorbing component(s) of that composition will absorb a portion of the IR light at very specific wavelengths. This phenomenon in turn enables the comparison of the energy spectrum with and without the IR-absorbing component(s), to obtain an absorption profile with patterns that can be used to identify the materials in composition. Additionally, the concentration of a material in the composition is directly measured by the amount of light that is absorbed by the material.

Early IR analyzers were spectrometers that used grating techniques or prisms to break IR radiation into its individual wavelengths. The individual energies would then be introduced into a gas cell by means of a moveable slit aperture and the radiation of the selected wavelength passing through the gas cell would be detected. Such dispersive IR analyzers used electronic processing means to correlate the slit aperture position with the IR energy level and the signal from the detector, and produce energy versus absorbance relations.

The principal drawbacks of dispersive spectrometers are the use of movable parts that are prone to failure, the cost of the spectrometer apparatus due to the number of components, and the slow collection rates that are characteristic of dispersive spectrometer operation.

Fourier transform IR (FT-IR) spectrometers, like dispersive spectrometers, also use broad energy IR sources. The originally generated IR beam is split into two beams and an interference pattern is created by sending one of the two beams in and out-of-phase, using a movable mirror. A laser beam is used to monitor the location of the movable mirror at all times. After the dual beam is sent to a sample, a sensor component of the spectrometer device receives the convoluted infrared wave pattern together with the laser-positioning beam. That information is then sent to a computer and deconvoluted using a Fourier transform algorithm. The energy versus mirror displacement data is thereby converted into energy versus absorbance relationships. The drawbacks of FT-IR spectrometers include their complexity and substantial cost.

Infrared thermopile detectors are employed in the practice of the present invention, and have the major advantages over dispersive and FT-IR spectrometers of (i) low cost, (ii) simplicity of design (no movable parts), (iii) fast response.

The thermopile-based infrared monitoring system of the invention comprises an infrared (IR) light source, a gas cell and a thermopile detector. The gas cell is a gas sample monitoring region, which in the broad practice of the invention may comprise any suitable compartment, passageway or chamber in which the gas to be monitored is subjected to passage of IR light through the gas for the purpose of using its IR absorbance-determined output to generate control signal(s) for process monitoring and control. The monitoring system in preferred practice utilizes mirror(s) and/or lenses to collimate and direct the IR light. The thermopile detector generates small voltages when exposed to IR light (or heat in the IR spectral regime). The output signal of the thermopile detector is proportional to the incident radiation on the detector.

Thermopile detectors employed in the preferred practice of the present invention have a multiple array of elements in each detector unit. For instance, in a dual element detector, one of the thermopile detector elements is used as a reference, sensing IR light in a range in which substantially no absorption occurs (e.g., wavelength of $4.00\pm0.02$ $\mu$m). The second thermopile detector element is coated with a filter that senses IR energy in the spectral range of interest (such spectral range depending on the particular material to be monitored). Comparison of the differences in the voltages generated by the reference thermopile detector element and those generated by the thermopile detector active element(s) provides a concentration measurement. Detectors with up to 4 thermopile detector element arrays are commercially available. For example, in a 4-element detector unit, one detector element is employed as a reference and the remaining 3 detector elements are utilized for measurements in different spectral regions.

A schematic representation of a thermopile-based detector system illustrating its operation is shown in FIG. 1, wherein IR source 10, such as an IR lamp, generates a broad (extended spectral range of IR wavelengths) infrared beam 12. The IR beam 12 is impinged on the gas cell 14 having an interior volume 16 in which the gas to be monitored is present for analysis. The gas cell may be a compartment, cross-sectional region or portion of a gas flow conduit in the semiconductor process system. Alternatively, a slip-stream (side stream) of a gas flow may be extracted from a flow conduit or process tool piping for the gas monitoring operation.

After passage through and interaction with the gas in the interior volume 16 of the gas cell 14, IR radiation 18 emitting from the gas cell 14 after traversing same then impinges on thermopile detector 20. The thermopile detector unit may utilize embedded IR filter(s) allowing the radiation of specific IR wavelengths to pass through the (respective) filter(s), in consequence of which the thermopile detector determines the radiation intensity and produces an output voltage signal for each element of the detector. The voltage output of the thermopile detector unit shown in FIG. 1 is passed by means of signal transmission line 22 to central processing unit 24, e.g., a personal computer, microprocessor device, or other computational means, wherein voltage signal(s) generated by the detector element(s) are algorithmically manipulated to produce an output concentration value for each of the gas component(s) of interest.

The thermopile-based analyzer system illustratively shown in FIG. 1 includes mirrors 26 and 28 for focusing the IR radiation. Mirrors can also be used to multipass the infrared beam more than one time across the interior volume 16 in order to enhance the detection limit. The infrared light source 10 in the FIG. 1 system may be of any suitable type, as for example a PerkinElmer IRL 715 infrared lamp providing IR radiation in a spectrum of from about 2 to about 4.6 $\mu$m wavelength. The thermopile detector 20 likewise may be of any suitable type, as for example a PerkinElmer TPS 3xx single detector, a PerkinElmer TPS 5xx single detector, a PerkinElmer 2534 dual detector, or a PerkinElmer 4339 quad detector, as necessary or desirable in a given end use application of the invention. Such illustrative infrared light source 10 and thermopile detector 20 elements are commercially available from PerkinElmer Optoelectronics (Wiesbaden, Germany).

Thermopile detector elements in one preferred embodiment of the invention have a response time in the 10–40 millisecond (ms) range. Thermopile detector units employed in the practice of the invention are advantageously configured with detector absorber areas for collecting the infrared light to be measured, with thermal elements positioned below the absorber area, so that infrared light incident on the absorber area heats the absorber area and generates a voltage at the output leads, as a DC voltage providing a direct measure of the incident radiation power. Such thermopile detector unit advantageously employs a gas-specific infrared radiation band pass filter in front of the thermopile detector element, so that the decrease in output voltage generated by such thermopile is directly related to the amount of infrared absorption by the corresponding gas. The thermopile detector unit as mentioned may include a multiplicity of absorber areas, including reference (unfiltered) absorber and gas-filtered absorber regions, with the latter filters being gas-specific for sensing of the semiconductor gases or gas components of interest (e.g., arsine, phosphine, germane, stibine, distibine, silane, substituted silanes, chlorine, bromine, organometallic precursor vapor, etc.).

In accordance with the invention, thermopile IR detector units are usefully employed for process control in semiconductor process applications, as described more fully below.

In one illustrative embodiment of the invention, the thermopile IR detector unit is employed as a gas delivery monitoring unit, e.g., as an in-line monitor installed in the gas delivery line of a semiconductor tool, to ensure delivery of an appropriate concentration of material into the tool chamber and/or flow circuitry. In such application, the inherent stability of the thermopile detector unit facilitates accurate concentration measurements. Use of the thermopile detector unit for such gas delivery sensing and control in turn minimizes the need to calibrate mass flow controllers used for metered delivery of the feed gas to the tool. Further, the signal generated by the thermopile detector unit enables feedback control arrangements to be implemented in the semiconductor process, e.g., involving feedback from the thermopile detector unit to the mass flow controller to responsively increase or decrease delivery rates so as to maintain constant concentration, volumetric flow rate, reagent flux, etc.

In another illustrative embodiment of the invention, a thermopile detector unit is utilized as an abatement tool controller for an abatement system for treating effluent produced in a semiconductor manufacturing operation, or other industrial process. For such purpose, the thermopile detector unit advantageously is installed at the inlet of an abatement apparatus, where the abatement apparatus receives the effluent to be treated. In such service, the thermopile detector unit is used to sense whether or not an upstream tool that generates the effluent in active on-stream operation, is in an active operating mode, or alternatively whether or not the upstream tool is in a non-effluent-producing state, e.g., undergoing purging or cleaning. The thermopile detector unit, by way of specific example, is usefully employed as an abatement tool controller for an effluent scrubber, such as a wet scrubber or a dry scrubber, whereby the presence of the thermopile detector unit transforms the scrubber into a "smart" scrubber and enhances the efficiency of the scrubber, allowing conservation of resources (lower consumables) to be achieved.

As another illustrative example, the thermopile detector unit is useful in an effluent abatement application for facilitating the switching of abatement equipment and/or abatement treatment methods, depending on the type of effluent being discharged from an upstream semiconductor process tool to an effluent abatement scrubber. For instance, when the thermopile detector unit detects a deposition material (e.g., silane, low-k material), the effluent gas stream could be sent by the monitoring and control system to an abatement tool most appropriate for abatement of the effluent from the deposition process (such as a thermal oxidation unit). When the thermopile detector unit does not sense the deposition material, it implies that the tool (e.g., an upstream vapor deposition chamber) is undergoing a cleaning step, and the gas stream then is sent to a different "best available tool" for abatement of the cleaning step effluent (e.g., a water scrubber).

As yet another illustrative example, the thermopile detector unit is usefully employed as an end point detector, which is installed downstream from a semiconductor process chamber. In such service, the analyzer serves as an in-line monitor to sense the concentration of species discharged from the process chamber as a function of time. Changes in the sensed concentration of the discharged effluent from the process chamber can be used to generate endpoint signals that can be sent to an tool operator, and/or to automatic process control equipment that responsively shuts down the apparatus or initiates post-processing steps such as purge, cleaning, etc.

Figure 2:
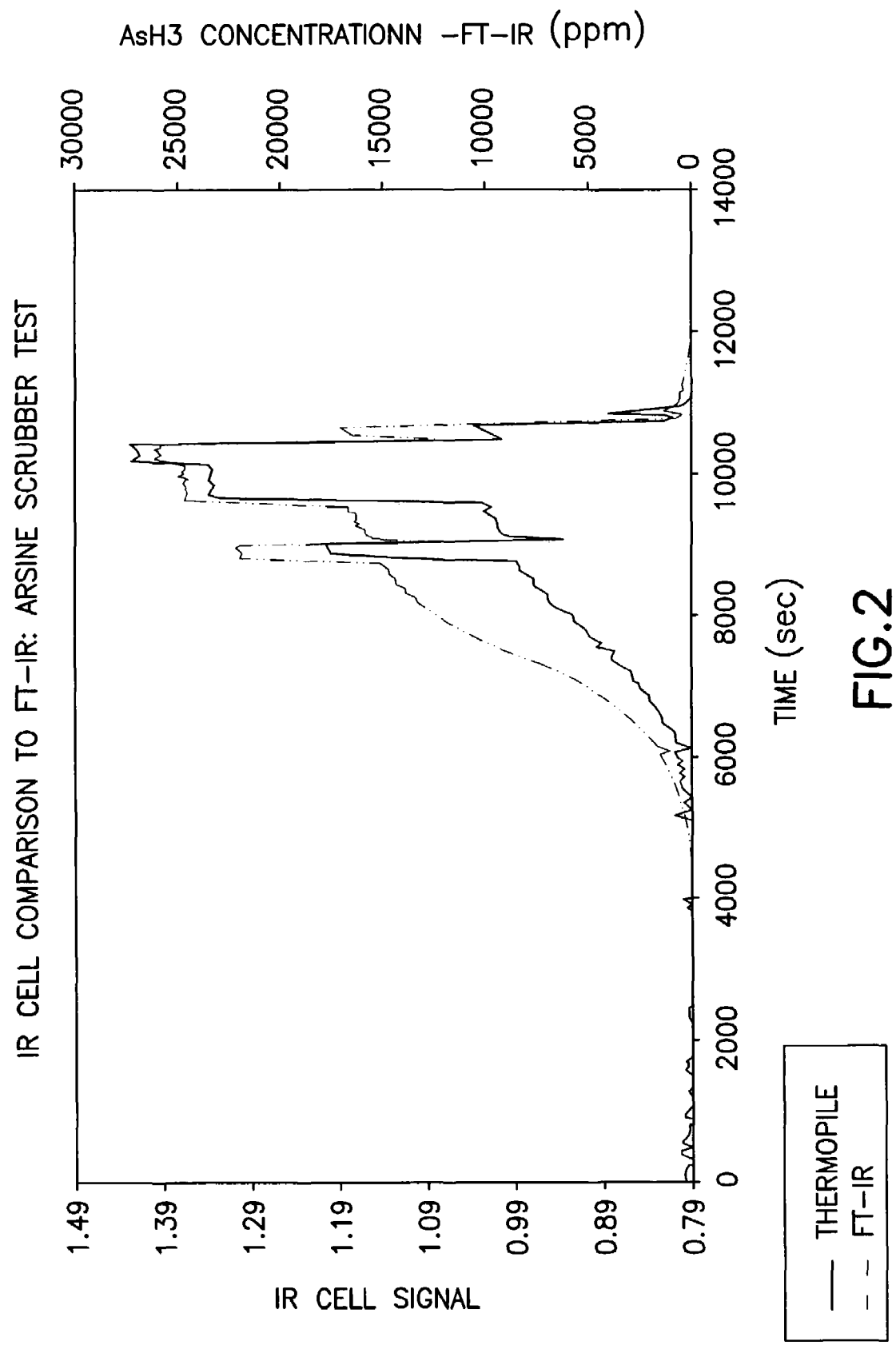
FIG. 2 is a graph of IR cell signal (curve A) and arsine concentration, FT-IR (ppm) (curve B) as a function of time, in seconds, for a thermopile detector in side-by-side service with an FT-IR spectrometer, monitoring arsine breakthrough in the exhaust of a dry scrubber test column.

FIG. 2 shows measurements collected using a thermopile detector unit in side-by-side service with an FT-IR spectrometer, to monitor arsine breakthrough at the exhaust of a dry scrubber test column. The arsine stream was simulative of the As-containing effluent produced by a semiconductor device structure arsenic doping process, or alternatively by a gallium arsenide epitaxial growth process. As shown by the curves in FIG. 2, the thermopile detector unit response (curve A) was faster than the FT-IR spectrometer signal (curve B), and the thermopile detector unit was capable of capturing the concentration changing trends.

Figure 3:
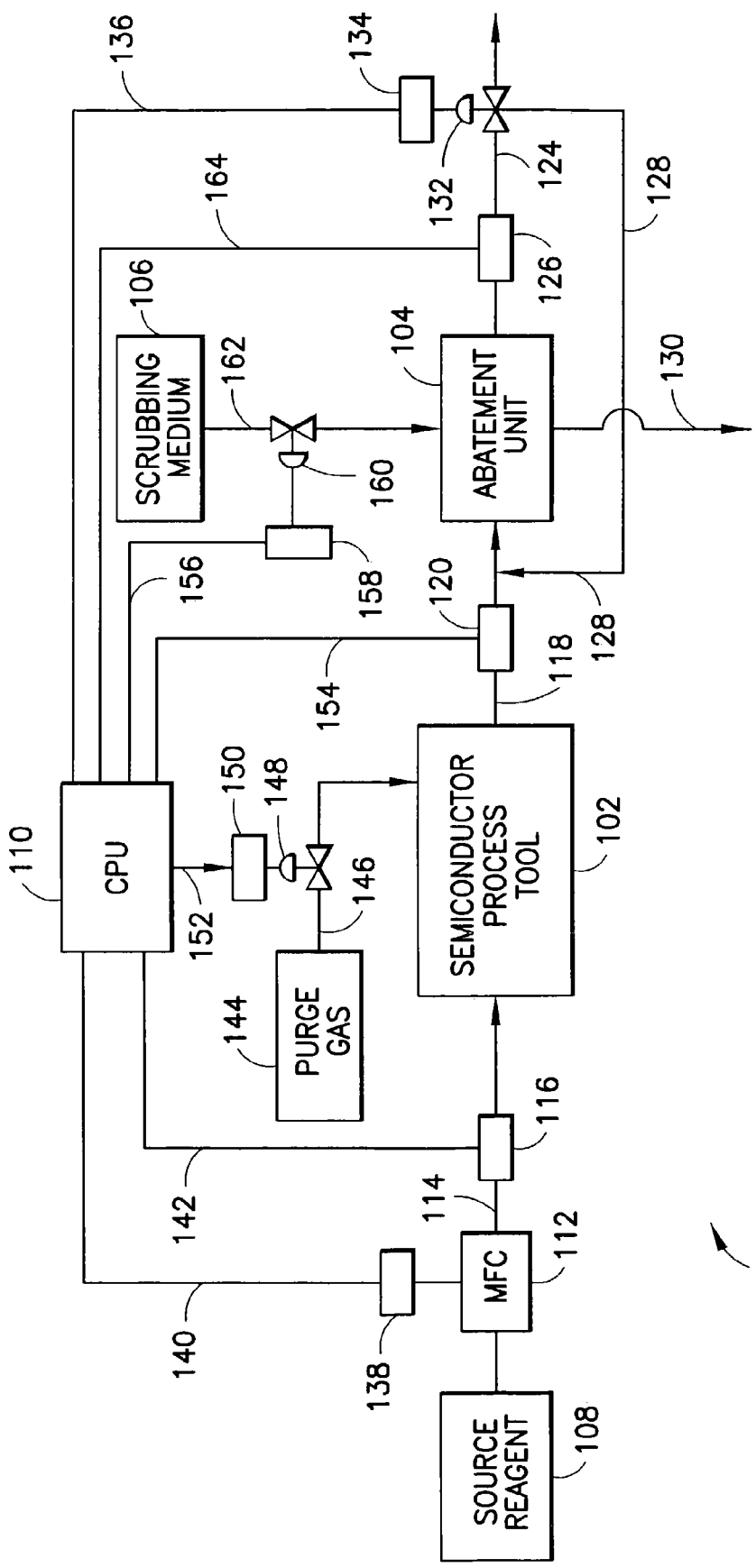
FIG. 3 is a schematic diagram of a semiconductor process facility, utilizing thermopile detectors for gas phase monitoring and control of process streams associated with a semiconductor process tool and abatement unit.

FIG. 3 is schematic representation of an exemplary semiconductor process system 100, including an illustrative semiconductor process tool 102 coupled with abatement unit 104 for abating effluent components that are of a toxic or hazardous character. The system includes a central processing unit (CPU) 110 for process monitoring and control utilizing various thermopile detector units, as hereinafter described in greater detail.

The semiconductor process tool 102, as shown, is arranged to receive a source reagent from source reagent supply 108. By way of examples, the semiconductor process tool 102 may illustratively comprise an epitaxial growth chamber, with the source reagent being a silane gas, or the semiconductor process tool 102 may illustratively comprise a chemical vapor deposition (CVD) chamber receiving an organometallic precursor from the source reagent supply 108, or the process tool 102 may illustratively comprise any other processing unit in a semiconductor manufacturing facility.

Source reagent from source reagent supply 108 flows in feed line 114 to the semiconductor process tool 102. Feed line 114 contains a mass flow controller 112 equipped with a mass flow controller set point adjusting unit 138, coupled to the mass flow controller in operative relationship thereto. A thermopile detector unit 116 is mounted in an in-line manner in feed line 114, and arranged for detection of the gaseous reagent flowed to the semiconductor process tool in such feed line 114. The gas concentration signal generated by the thermopile device 116 is transmitted in signal transmission line 142 to the CPU 110. The CPU 110 may in turn be arranged in controlling relationship, by means of control signal line 140 to the mass flow controller set point adjusting unit 138, which in turn controls the set point of mass flow controller 112.

In this manner, the set point of the mass flow controller may be modulated in respect to the concentration sensed by the thermopile detector 116, to responsively adjust the set point of the mass flow controller by adjusting unit 138, so that mass flow controller 112 provides a precision set point flow of the source reagent to the semiconductor process tool.

In the FIG. 3 system, the semiconductor process tool 102 produces an effluent that is flowed in effluent discharge line 118 to the abatement unit 104 for treatment to produce a treated effluent of appropriate character, which is discharged from the abatement unit 104 in abatement unit discharge line 124.

The semiconductor process tool effluent discharge line 118 as shown contains a thermopile detector unit 120 mounted therein, for sensing concentration of desired effluent gas component(s). The thermopile detector unit 120 responsively generates a concentration sensing signal that is transmitted in signal transmission line 154 to CPU 110.

In response to the sensing by thermopile detector unit 120 of the selected component(s) in the effluent stream in effluent discharge line 118, the CPU 110 can correlatively adjust the set point of mass flow controller 112, by a modulation of set point adjusting unit 138. Alternatively, the CPU 110 in response to the sensed concentration in the effluent discharge stream, as sensed by thermopile detector unit 120, may terminate flow of source reagent to the semiconductor process tool 102, such as by closure of a flow control valve (not shown) in feed line 114, and/or effect other operations that modulate or terminate processing steps involving the semiconductor process tool 102.

For example, the effluent gas sensing by thermopile detector unit 120 may be employed to effect changeover of the semiconductor process tool 102 from an active processing mode to a cleaning mode, or from a first active processing step to a subsequent processing step. By way of specific example, the concentration sensed by thermopile detector unit 120 for the component of interest in the effluent stream in discharge line 118, may be employed to generate a corresponding concentration signal transmitted in signal transmission line 154 to CPU 110. The concentration signal may indicate that the active processing step is satisfactory completed. The CPU 110 then terminates the active flow of source reagent from source reagent supply 108 to the tool, as previously described. Concurrently, the CPU may send a control signal in control signal transmission line 152 to the valve controller 150. The valve controller 150 is coupled in controlling relationship to flow control valve 148 in the purge gas feed line 146 connected to purge gas supply 144. The control signal from the CPU 110 thereby actuates the valve controller 150, which in turn causes valve 148 to open, and purge gas to flow through the semiconductor process tool 102.

In this manner, the process tool is efficiently purged of source reagent gases, and readied for subsequent active processing, or alternatively readied for cleaning steps preceding subsequent active (on-stream) processing. When the purge gas has been flowed through the process tool to sufficient extent to remove the source reagent residues, decomposition by-products, etc., as indicated by corresponding concentration sensing by the thermopile detector unit 120 and transmission of the associated concentration signal in signal transmission line 154 to CPU 110, the CPU actuates the valve controller 150 to shut valve 148 and terminate purge gas flow to the process tool.

In lieu of, or in addition to, the provision of thermopile detector unit 116 in gas feed line 114 to the semiconductor process tool 102, the system may utilize the thermopile detector unit 120 in the effluent discharge line 118 for monitoring and control of the semiconductor process tool 102.

Additionally, or alternatively, the thermopile detector unit 120 upstream of abatement unit 104 may be constructed and arranged to monitor and responsively control the abatement unit 104.

The abatement unit 104 illustratively shown in FIG. 3 can be of any of various types, and can include multiple abatement treatment steps and constituent process units, e.g., wet scrubbers, dry scrubbers, thermal oxidation units, catalytic oxidation units, chemisorption units, physical adsorption systems, etc.

For purposes of illustration, the abatement unit 104 is shown in FIG. 3 as comprising a wet scrubbing unit, by means of which the effluent discharged from the semiconductor process tool 102 in discharge line 118 is subjected to wet scrubbing. The wet scrubbing is carried out in scrubber abatement unit 104 with a suitable liquid scrubbing medium, e.g., water, acidic aqueous solution, basic aqueous solution, etc., supplied from scrubbing medium source 106 and flowed in scrubbing medium feed line 162 to the abatement unit 104.

The flow rate of scrubbing medium in line 162 is controlled by flow control valve 160, operatively coupled with valve controller 158, which in turn is actuated by means of a control signal transmitted via signal transmission line 156 from CPU 110.

The thermopile detector unit 120 therefore is usefully arranged to sense concentration of a component to be abated in the abatement unit 104, and to responsively transmit a signal correlative of such concentration to CPU 110 in signal transmission line 154. In response to such signal indicative of the concentration of component to be abated in the effluent stream, the CPU 110 programmatically transmits a control signal in control signal transmission line 156 to valve controller 158, which modulates the setting of flow control valve 160 to flow a desired amount of scrubbing medium to the abatement unit 104 for contacting with the effluent, to thereby abate the scrubbable component of interest in the effluent stream.

Thus, the sensing of a relatively lower concentration of scrubbable component in the effluent stream by thermopile detector unit 120 will cause the CPU 110 to actuate the valve controller 158 to reduce the flow of scrubbing medium to the abatement unit 104, so that the scrubbing medium is provided in an amount and at a rate that is appropriate to the amount of scrubbable component to be removed. The scrubbing medium containing the scrubbed component then is discharged from the abatement unit 104 in scrubbing medium discharge line 130.

In an analogous manner, the treated effluent discharged from abatement unit 104 in effluent discharge line 124 may be monitored by thermopile detector unit 126, which transmits a corresponding concentration signal in signal transmission line 164 to CPU 110. The CPU 110 thereupon programmatically responds to the sensed concentration value by modulating the flow control valve 160 via valve controller 158, as previously described, to increase, maintain or decrease the scrubbing medium flow rate, as necessary to achieve a predetermined low level of scrubbable component in the final effluent discharged from the scrubber abatement unit 104 in discharge line 124. Such predetermined low level of the scrubbable component may for example be a concentration that is below the lower detection limit of the thermopile detector unit 126.

In addition to modulating the flow of scrubbing medium to ensure that the desired extent of removal of the scrubbable component is achieved, the concentration of the scrubbable component sensed by thermopile detector unit 126 may be transmitted to CPU 110 in signal transmission line 164, to responsively actuate recirculation of effluent from discharge line 124 to the inlet of the abatement unit 104, in line 128.

Line 128 is coupled to 3-way valve 132 disposed in discharge line 124. Valve controller 134 is operatively coupled with 3-way valve 132. Valve controller 134 is joined by control signal transmission line 136 to CPU 110. By this arrangement, the concentration of the scrubbable component in the effluent from the abatement unit 104 is sensed by thermopile detector unit 126 and the concentration signal sent to CPU 110 by signal transmission line 164. The CPU 110 responsively sends a control signal in signal transmission line 136 to the valve controller 134 coupled with 3-way valve 132, whereby the valve 132 is adjusted so that treated effluent from discharge line 124 is recirculated in line 128 to line 118, for reintroduction to abatement unit 104.

In such manner, the recycle rate, as well as the scrubbing medium flow rate, are controllable to maximize removal efficiency of scrubbable components in the abatement unit 104.

It will be apparent from the preceding discussion of the illustrative embodiment of FIG. 3, that thermopile detector units may be variously employed in a semiconductor manufacturing facility to monitor gas concentrations and responsively control fluid flow rates and/or other process conditions and/or operational aspects of the semiconductor process, so that process efficiency is maximized, process reagent requirements are minimized, and product consistency is more effectively achieved, relative to a corresponding semiconductor manufacturing facility lacking such thermopile detector monitoring and control means.

Further, although the embodiment of FIG. 3 has been described generally for a single gas component of interest (as the monitored gas species), it will be appreciated from the discussion earlier herein that multi-component thermopile detectors may be advantageously employed, which function to sense the concentrations of multiple gas components in multicomponent process streams.

Further, although the invention has been illustratively described with reference to a single semiconductor process tool, it will be recognized that a semiconductor processing facility in conventional practice is comprised of a multiplicity of tools and process system componentry, and therefore that thermopile detector units may be utilized concurrently with a multiplicity of detector units in various locations of the semiconductor process, e.g., in specific chambers or regions of the process system flow circuitry, and that the IR thermopile detector units may be integrated with control circuitry involving one or multiple computers, processors, cycle-time program controllers, etc. Further, it will be recognized that the thermopile detectors in producing voltage output signals may be utilized with other signal generation and transmission/control devices and interfaces, to effectuate the process monitoring and control functions needed in a specific operation.

For example, the thermopile detector output signal may be converted to a radio frequency signal transmitted by a radio frequency transponder that is transmitted to a radio frequency receiver in an integrated wireless network for monitoring and control purposes.

The voltage-based output of the thermopile detector may be converted to other signal forms, or even reconverted to an infrared control signal for wireless communication to a central processing unit or other computational or control means.

The features, aspects and advantages of the present invention are further shown with reference to the following non-limiting examples relating to the invention.

EXAMPLE

Thermopile Detector System Experimental Using Trimethyl Silane

Figure 4:
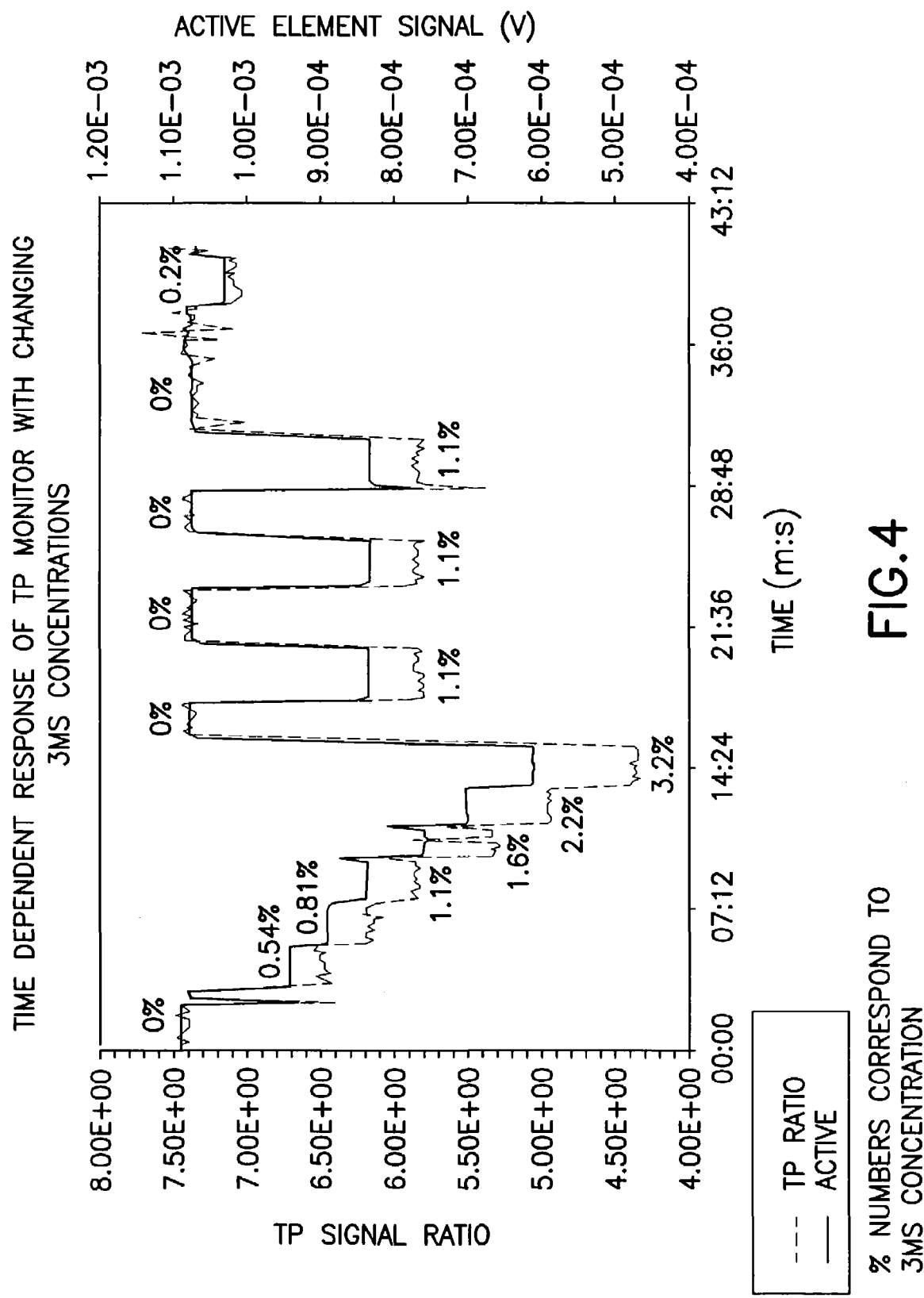
FIG. 4 is a graph showing the response of a thermopile detector system as a function of different trimethyl silane concentrations.

FIG. 4 demonstrates the response of a thermopile detector system as a function of different trimethyl silane concentrations. Trimethyl silane is a candidate material for thermopile-based process monitoring applications as it is used as low-k precursor in semiconductor processes. This specific system includes a dual sensor thermopile detector. The active element filters all IR light with the exception of the methyl group (around 3000 cm-1). The second filter measures a narrow band around 2500 cm-1 and is used as a reference. In FIG. 4, the curve labeled "TP ratio" depicts the response of the active element divided by the signal generated by the reference element. The curve labeled "active" corresponds to the voltage generated by only the active detector element. FIG. 4 also demonstrates the stability and repeatability of the monitoring system.

Figure 5:
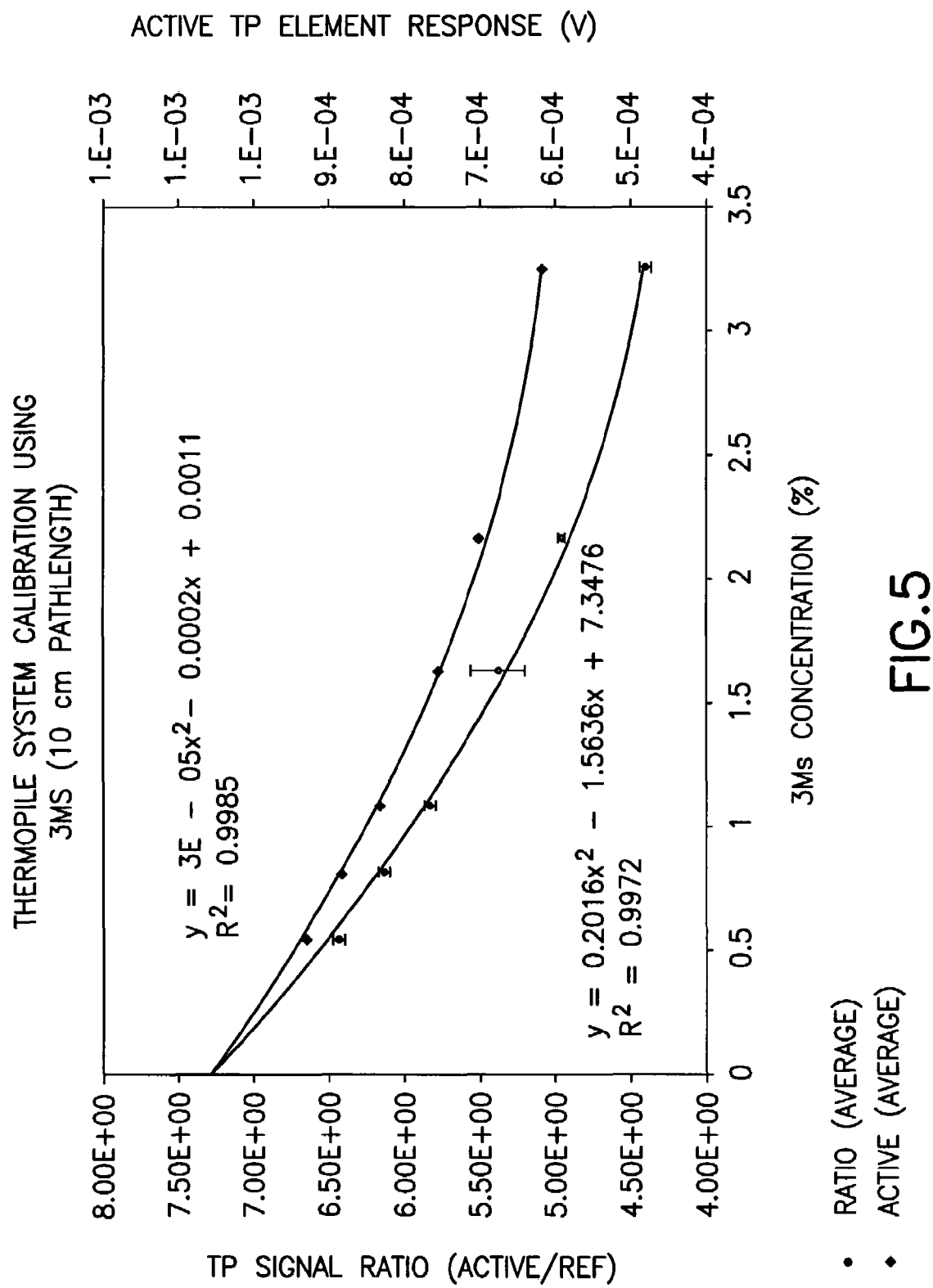
FIG. 5 is a graph showing a calibration curve for trimethyl silane based on the information depicted in FIG. 4.

FIG. 5 shows a graph of a calibration curve for trimethyl silane, based on the information depicted in FIG. 4. Similar to FIG. 4, one calibration curve corresponds to the ratio between the active and reference signals, while the other curve corresponds to the signal generated by the active detector element. The curves were fitted to a second order polynomial with a greater than 0.999 correlation coefficient. Based on such calibration curve, a detection limit of 500 parts per million (ppm) was estimated.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. A method of operating a semiconductor process including processing of or with a gas, said method comprising transmitting infrared radiation through the gas for infrared radiation absorbance by a desired component of said gas, detecting the infrared radiation transmitted through the gas with a thermopile detector, generating an output from said thermopile detector indicative of concentration of said selected component of said gas, and controlling one or more conditions in and/or affecting the semiconductor process, in response to said output.

2. The method of claim 1, wherein the one or more conditions in and/or affecting the process include flow rate of a chemical reagent to a semiconductor process tool.

3. The method of claim 1, wherein the one or more conditions in and/or affecting the process include flow rate of a gas stream discharged from or flowed to a process unit in the semiconductor process.

4. The method of claim 3, wherein the gas stream to a semiconductor process tool is monitored.

5. The method of claim 3, wherein the gas stream flowed to an abatement unit is monitored.

6. A method of operating a semiconductor process including processing of or with a gas, said method comprising sensing concentration of a desired component of said gas with a thermopile detector, generating an output from said thermopile detector indicative of concentration of said selected component of said gas, and controlling one or more conditions in and/or affecting the semiconductor process, in response to said output, wherein the one or more conditions in and/or affecting the process include flow rate of a gas stream discharged from or flowed to a process unit in the semiconductor process, and wherein the gas stream discharged by an abatement unit is monitored.

7. The method of claim 1, wherein the thermopile sensor output is employed to modulate a valve.

8. The method of claim 1, wherein the thermopile detector output is employed to modulate a set point of a mass flow controller.

9. A method of operating a semiconductor process including processing of or with a gas, said method comprising sensing concentration of a desired component of said gas with a thermopile detector, generating an output from said thermopile detector indicative of concentration of said selected component of said gas, and controlling one or more conditions in and/or affecting the semiconductor process, in response to said output, wherein the thermopile detector output is employed to modulate flow of a scrubbing medium in an abatement treatment step of the process.

10. The method of claim 1, wherein the thermopile detector output is employed to terminate a first process step and initiate a second process step.

11. A method of operating a semiconductor process including processing of or with a gas, said method comprising sensing concentration of a desired component of said gas with a thermopile detector, generating an output from said thermopile detector indicative of concentration of said selected component of said gas, and controlling one or more conditions in and/or affecting the semiconductor process, in response to said output, wherein the thermopile detector output is employed to modulate recycle of a fluid stream in the process.

12. A method of operating a semiconductor process including processing of or with the material, said method comprising transmitting infrared radiation through the material for infrared radiation absorbance by a desired component of said material, detecting the infrared radiation transmitted through the material with a thermopile detector, generating an output from sent thermopile indicative of concentration of said selected component of said material, and controlling one or more conditions in and/or affecting the semiconductor process, in response to said output.

13. The method of claim 12, wherein the material comprises a solid.

14. The method of claim 12, wherein the material comprises a fluid.

15. The method of claim 12, wherein the material comprises a liquid.

16. The method of claim 12, wherein the material comprises a gas.

* * * * *